(12) United States Patent
Reaume et al.

(10) Patent No.: US 9,408,844 B2
(45) Date of Patent: *Aug. 9, 2016

(54) METHODS FOR TREATING INFLAMMATORY CONDITIONS

(71) Applicant: Melior Discovery, Inc., Exton, PA (US)

(72) Inventors: Andrew Reaume, Exton, PA (US); Heather Hain, Exton, PA (US); Michael S. Saporito, Exton, PA (US)

(73) Assignee: Melior Discovery, Inc., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/254,947

(22) Filed: Apr. 17, 2014

(65) Prior Publication Data

US 2014/0227209 A1    Aug. 14, 2014

Related U.S. Application Data

(63) Continuation of application No. 11/937,680, filed on Nov. 9, 2007, now Pat. No. 8,716,294.

(60) Provisional application No. 60/865,315, filed on Nov. 10, 2006.

(51) Int. Cl.
*A61K 31/497* (2006.01)
*A61K 31/496* (2006.01)

(52) U.S. Cl.
CPC ............. *A61K 31/496* (2013.01); *A61K 31/497* (2013.01)

(58) Field of Classification Search
None
See application file for complete search history.

(56) References Cited

U.S. PATENT DOCUMENTS 6,608,094 B2    8/2003    Sankaranarayanan

FOREIGN PATENT DOCUMENTS

WO    2006072175 A1    7/2006
WO    2008101692 A1    8/2008

OTHER PUBLICATIONS

Black et al (BMC Pulmonary Med 4:1-7, 2004).*
Shoda et al (Endocrinology 138:1886-1892, 1997).*
Campo et al., Expression of Receptor for Advanced Glycation End Products in Sarcoid Granulomas, Am J Respir Crit Care Med, (2007), 175:498-506.
Colaco et al., The role of the Maillard reaction in other pathologies: Alzheimer's disease, Nephrol Dial Transplant, (1996), 11(Suppl 5):7-12. Abstract only.
Dierks et al., Influence of Tenilsetam on AEP-P300 in Alzheimer's disease, J Neural Transm, (1989), [P-D Sect], 1:49.
Hinshaw et al., Hypersensitivity Reactions, Delayed—http://emedicine.medscape.com (Mortality/Morbidity Section, viewed online Jul. 30, 2009.
Münch et al., The cognition-enhancing drug tenilsetam is an inhibitor of protein crosslinking by advanced glycosylation, J Neural Transm, (1994), [P-D Sect], 8(3):193-208.
Nakamura et al., Circulating levels of advanced glycation end products (AGE) and interleukin-6 (IL-6) are independent determinants of serum asymmetric dimethylarginine (ADMA) levels in patients with septic shock, Pharm Res, (2009).
Reddy et al., Inhibitors of the Maillard reaction and AGE breakers as therapeutics for multiple diseases, Drug Discov Today, (Jul. 2006), 11(13-14):646-654. Abstract only.
Sander et al., Oxidative Stress, Irritant Dermatitis, (2006), Ch 40: 375-382.
Senaldi et al., Protective Effect of N-Acetylcysteine in Hapten-Induced Irritant and Contact Hypersensitivity Reactions, J Invest Dermatol, (1994), 102:934-937.
Shoda et al., Inhibitory Effects of Tenilsetam on the Maillard Reaction, Endocrinology, (May 1997), 138(5):1885-1895.
The Merriam Webster Online Dictionary (accessed online on Jul. 30, 2009).
Tsukahara et al., High Levels of Urinary Pentosidine, an Advanced Glycation End Product, in Children With Acute Exacerbation of Atopic Dermatitis: Relationship With Oxidative Stress, Metabolism, (2003), 52(12):1601-1605.
Aisen et al., Inflammation and Alzheimer disease, Mol Chem Neuropathol, (May-Aug. 1996), 28(1-3):83-88.

* cited by examiner

*Primary Examiner* — Craig Ricci
(74) *Attorney, Agent, or Firm* — Pepper Hamilton LLP

(57) ABSTRACT

The present invention relates to compounds and pharmaceutically acceptable salts thereof and formulations comprising tenilsetam or pharmaceutically acceptable salts thereof that are useful in modulating inflammation. In particular, the compounds or pharmaceutically acceptable salts thereof are useful for treating or preventing a disease or disorder involving inflammation, including, but not limited to, delayed type hypersensitivity and contact hypersensitivity.

23 Claims, 3 Drawing Sheets

METHODS FOR TREATING INFLAMMATORY CONDITIONS

FIELD OF THE INVENTION

The present invention is directed to methods of preventing or treating an inflammatory disease or condition in a mammal comprising administering a tenilsetam-related compound.

BACKGROUND OF THE INVENTION

Delayed-type hypersensitivity (DTH) reactions are antigen-specific cell-mediated immune responses that can mediate harmful (e.g., allergic dermatitis and autoimmunity) aspects of immune function. The immune reaction is characterized by swelling at the site of challenge and by an infiltration of monocytes/macrophages and lymphocytes into the epidermis and dermis. Type IV or DTH, is most seriously manifested when antigens (for example those of tubercle bacilli) are trapped in a macrophage and cannot be cleared. T cells are then stimulated to elaborate lymphokines which mediate a range of inflammatory responses. Other aspects of DTH reactions are seen in graft rejection and allergic contact dermatitis. DTH is used as a general category to describe all those hypersensitivity reactions which take more than 12 hours to develop, and which involve cell-mediated immune reactions rather than humoral immune reactions. Whereas allergic reactions occur within seconds and minutes and immune complex reactions occur within several hours to one day, DTH reactions peak at 2 to 3 days.

Unlike other forms of hypersensitivity, type IV hypersensitivity cannot be transferred from one animal to another by serum, but can be transferred by T cells (TH1 cells in mice). In humans, transfer from a sensitized to a non-sensitized individual can be also achieved only by T lymphocytes and, interestingly, by a low molecular weight material extracted from them (transfer factor). DTH is associated with T cell protective immunity but does not necessarily run parallel with it—there is not always a complete correlation between delayed hypersensitivity and protective immunity. The T cells necessary for producing the delayed response are cells which have become specifically sensitized to the particular antigen by a previous encounter, and they act by recruiting other cell types to the site of the reaction.

Three types of delayed hypersensitivity reaction are recognized: Contact hypersensitivity and tuberculin-type hypersensitivity both occur within 72 hours of antigen challenge, whereas granulomatous reactions develop over a period of weeks. The granulomas are formed by the aggregation and proliferation of macrophages, and may persist for weeks. This reaction is, in terms of its clinical consequences, by far the most serious type of DTH response. The position is complicated because these different types of reaction may overlap, or occur sequentially following a single antigenic challenge.

The DTH reactions are likely important for host defense against intracellular parasites such as tuberculosis and certain viruses and are prevalent in certain disease such as sarcoidosis, Wegener's granulomatosis, and polymyositis. In some diseases, such as chronic granulomatous disease of childhood, granuloma formation can lead to obstruction of vital structures such as the esophagus or ureters.

Contact hypersensitivity, or contact dermatitis, is a T cell-mediated cutaneous immune/inflammatory reaction to haptens. Typical manifestations of contact dermatitis include, but are not limited to, rashes, dermatoses, and skin eruptions, which can be treated topically to improve or favorably alter the disease condition. Such rashes, dermatoses or skin eruptions include acute, inflammatory reactions of the skin caused by an allergic or irritant reaction (such as that caused by, for example, poison ivy, poison oak or poison sumac, or other forms of allergic or irritant contact dermatitis), other forms of eczema, lichen simplex chronicus, rashes, dermatoses or skin eruptions of a chronic nature (such as, for example, seborrheic dermatitis, psoriasis, atopic dermatitis) or caused by infection, irritation or aggravation of another condition such as occurs with acne, and other rashes, dermatoses or skin eruptions.

Contact dermatitis may be produced by primary irritants or allergic sensitizes. Irritant contact dermatitis is a nonallergic reaction of the skin caused by exposure to irritating substances. Most primary irritants are chemical substances, although physical and biologic (infectious) agents may produce the same reaction. Irritants account for 80% of occupational contact dermatitis and also cause the most frequent type of non-industrial contact reaction. Allergic contact dermatitis is a manifestation of delayed hypersensitivity and results from the exposure of sensitized individuals to contact allergens. Poison ivy and poison oak induce sensitization in more than 70% of the population, thereby causing allergic contact dermatitis (Arndt, Kenneth A., Manual of Dermatologic Therapeutics, 5th edition, 1995, Little, Brown and Co., page 49).

Irritants may cause an inelastic and stiff-feeling skin, discomfort due to dryness, pruritus secondary to inflammation, and pain due to fissures, blisters, and ulcers. Mild irritants produce erythema, microvesiculation, and oozing that may be indistinguishable from allergic contact dermatitis. Chronic exposure to mild irritants or allergens results in dry, thickened, and fissured skin. Strong irritants cause blistering, erosion, and ulcers of the skin. Allergic contact dermatitis, in its mild form, is similar in appearance to the irritant eruption. A more typical allergic contact reaction may consist of grouped or linear tense vesicles and blisters. If involvement is severe there may be marked edema, particularly of the face and in the periorbital and genital areas.

Generally, eczematous dermatitides include a group of diseases which present with a common morphology: erythematous and papulovesicular when acute; erythematous and scaling (with or without fissures and lichenification) when chronic. Included under this rubric are atopic dermatitis, contact dermatitis, nummular dermatitis, seborrheic dermatitis and stasis dermatitis.

Atopic dermatitis is a common infantile eczema which affects approximately 10-20% of children in the United States. The disease has a strong association with allergic rhinitis and asthma and occurs in approximately one-third of children with a personal or family history of these disorders. Although IgE antibodies may be elevated in up to 80% of individuals with atopic dermatitis, the skin manifestations do not seem to be a purely IgE-mediated process. The etiology of atopic dermatitis is unknown. Current hypotheses have concentrated on the possibility that an aberrant T cell response, perhaps to staphylococcal superantigen, results in the activation of $T_H2$ cells.

Clinically, atopic dermatitis has been called the "itch that rashes." Pruritus is a hallmark of the disease. Infants less than 18 months of age typically present with an acute to subacute dermatitis which may involve the scalp, the face (particularly the cheeks), the posterior neck, the trunk and the extensor aspects of the extremities. After approximately two years of age, most individuals will present with a more chronic, lichenified and scaling form of the disease distributed about the face, neck, trunk and especially the flexural aspects of the extremities (antecubital and popliteal fossae). The reason for the change in distribution of the dermatitis on the extremities is not clear. Individuals with atopic dermatitis are prone to develop secondary infection with staphylococcal organisms, as well as with viruses and fungi. When the disease is flaring, these secondary infections must be excluded.

Contact Dermatitis, also described above, can be broken down into two main areas: irritant contact dermatitis and allergic contact dermatitis.

Irritant contact dermatitis is the direct result of injury to the skin caused by chemical exposure. Irritation can be further subdivided into acute corrosion (caused by a single exposure to strong acids and alkalis), acute irritation (caused by a single exposure to chemicals such as strong solvents and non-corrosive acids and bases), cumulative irritation (the most typical and caused by repeated exposures particularly to surfactants and emulsifiers) and phototoxicity (caused by exposure to irritating chemicals which require light for their activation). The clinical presentation of irritation can therefore vary from the acute onset of a third degree chemical burn (corrosion following phenol exposure) to the chronic scaling and xerotic dermatitis of "dishpan hands." Because irritant contact dermatitis is a function of the chemical, it will occur in all individuals exposed to this chemical given sufficient exposure times and concentrations. Nonetheless, it is clear that the skin of some individuals is much more irritable than others. The determinants of hyperirritable skin are numerous and include age, genetics, ambient environment, underlying skin disease(s), and concomitant chemical exposure.

Allergic contact dermatitis (ACD) develops following exposure to chemicals to which the individual has previously become sensitized. It is a type IV or delayed-type hypersensitivity reaction of the skin. There are over 3,000 environmental allergens which have been reported to cause this condition. The prevalence of ACD varies with the allergen. Typically, the patient will develop an erythematous, scaling, papulovesicular dermatitis at the sites of contact with the allergen. Long-standing, low grade allergens can create a more subacute to chronic, scaling lichenified dermatitis.

Nummular dermatitis is characterized by its "coin-shaped" lesions. As with other dermatitides, the acute form is papulovesicular whereas the chronic form is scaly and lichenified. Mild to severe pruritus accompanies the disease which most frequently affects men, typically in the sixth decade or beyond. The prevalence of the disease is unknown, but it would appear to be lower than that for most of the other eczemas.

Seborrheic dermatitis is one of the most common cutaneous diseases and affects from 3 to 5% of the population. One proposed etiology is overgrowth of *Pityrosporum*, a yeast that normally inhabits sebaceous skin (e.g., scalp, eyebrows, central face). The disease has two peaks, one in infancy and the other post-pubertal. Infantile seborrheic dermatitis typically occurs within the first months of life and affects the scalp ("cradle cap") and intertriginous areas with scales and crust. The skin about the ears and the neck may also be involved. In contrast, seborrheic dermatitis in adults typically involves the scalp, face, neck, mid upper chest and intertriginous zones (axillae, groin, submammary, and in obese patients beneath the pannus). On the face, it particularly concentrates about the eyebrows, nasolabial folds and retroauricular areas.

Stasis dermatitis is an eczematous process of the skin of the lower extremities which results from non-specific inflammation presumably induced by the leakage of serum secondary to venous hypertension. The disease is particularly common over the medial and anterior aspects of the shin and malleolar areas. When significant inflammation occurs, it can be accompanied by a secondary autosensitization dermatitis referred to as an "id."

SUMMARY OF THE INVENTION

The present invention provides methods of treating an inflammatory disease or condition in a mammal comprising administering to the mammal a therapeutically effective amount of a compound of formula I

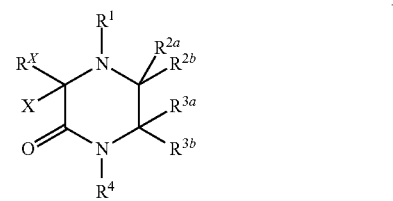

wherein: X is 2-thienyl, 3-thienyl, 2-furyl, 3-furyl, or phenyl, each unsubstituted, mono-substituted, di-substituted, or tri-substituted with, independently, OH, halogen, $C_1$-$C_4$ alkyl, $C_1$-$C_4$ alkoxy, or ($C_1$-$C_4$)alkoxy-($C_1$-$C_4$) alkyl; $R^1$ and $R^4$ are, independently, H or $C_1$-$C_4$ alkyl; $R^{2a}$ and $R^{2b}$ are, independently, H, OH, or $C_1$-$C_4$ alkyl, or, together, $R^{2a}$ and $R^{2b}$ are C=O; $R^{3a}$ and $R^{3b}$ are, independently, H, OH, or $C_1$-$C_4$ alkyl, or, together, $R^{3a}$ and $R^{3b}$ are C=O; and $R^X$ is H, $C_1$-$C_4$ alkyl, $C_1$-$C_4$ alkoxy, or ($C_1$-$C_4$) alkoxy-($C_1$-$C_4$) alkyl; or a pharmaceutically acceptable salt thereof.

In some embodiments, X is 2-thienyl, 3-thienyl, 2-furyl, or 3-furyl, each unsubstituted, mono-substituted, di-substituted, or tri-substituted with, independently, OH, halogen, $C_1$-$C_4$ alkyl, $C_1$-$C_4$ alkoxy, or ($C_1$-$C_4$) alkoxy-($C_1$-$C_4$) alkyl. In some embodiments, X is 2-thienyl, 3-thienyl, 2-furyl, or 3-furyl, each unsubstituted, mono-substituted, or di-substituted with, independently, OH, halogen, $C_1$-$C_4$ alkyl, or $C_1$-$C_4$ alkoxy. In some embodiments, X is 2-thienyl or 2-furyl, each unsubstituted, mono-substituted, or di-substituted with, independently, OH, halogen, or $C_1$-$C_4$ alkyl. In some embodiments, X is unsubstituted 2-thienyl or 2-thienyl mono-substituted with OH, halogen, or $C_1$-$C_4$ alkyl. In some embodiments, X is unsubstituted 2-thienyl.

In some embodiments, $R^1$ and $R^4$ are H. In some embodiments, $R^1$ and $R^4$ are $C_1$-$C_4$ alkyl.

In some embodiments, $R^{2a}$ and $R^{2b}$ are, independently, H or $C_1$-$C_4$ alkyl, or, together, $R^{2a}$ and $R^{2b}$ are C=O. In some embodiments, $R^{2a}$ and $R^{2b}$ are, independently, H or OH. In some embodiments, $R^{2a}$ and $R^{2b}$ are both H.

In some embodiments, $R^{3a}$ and $R^{3b}$ are, independently, H or $C_1$-$C_4$ alkyl, or, together, $R^{3a}$ and $R^{3b}$ are C=O. In some embodiments, $R^{3a}$ and $R^{3b}$ are, independently, H or OH. In some embodiments, $R^{3a}$ and $R^{3b}$ are both H.

In some embodiments, $R^X$ is H, $C_1$-$C_4$ alkyl, or $C_1$-$C_4$ alkoxy. In some embodiments, $R^X$ is H or $C_1$-$C_4$ alkyl. In some embodiments, $R^X$ is H.

In some embodiments, X is 2-thienyl or 2-furyl, each unsubstituted, mono-substituted, or di-substituted with, independently, OH, halogen, or $C_1$-$C_4$ alkyl; $R^{2a}$ and $R^{2b}$ are, independently, H or OH; $R^{3a}$ and $R^{3b}$ are, independently, H or OH; and $R^X$ is H.

In some embodiments, X is unsubstituted 2-thienyl or 2-thienyl mono-substituted with OH, halogen, or $C_1$-$C_4$ alkyl; $R^1$ and $R^4$ are, independently, H or $C_1$-$C_4$ alkyl; $R^{2a}$ and $R^{2b}$ are, independently, H or OH; $R^{3a}$ and $R^{3b}$ are, independently, H or OH; and $R^X$ is H.

In some embodiments, X is unsubstituted 2-thienyl or 2-thienyl mono-substituted with OH, halogen, or $C_1$-$C_4$ alkyl; $R^1$ and $R^4$ are H; $R^{2a}$ and $R^{2b}$ are, independently, H or OH; $R^{3a}$ and $R^{3b}$ are, independently, H or OH; and $R^X$ is H or halogen.

In some embodiments, X is unsubstituted 2-thienyl or 2-thienyl mono-substituted with OH, halogen, or $C_1$-$C_4$ alkyl; and $R^1$, $R^4$, $R^{2a}$, $R^{2b}$, $R^{3a}$, $R^{3b}$, and $R^X$ are H.

In some embodiments, X is unsubstituted 2-thienyl; $R^1$ and $R^4$ are, independently, H or $C_1$-$C_4$ alkyl; $R^{2a}$ and $R^{2b}$ are, independently, H or OH; $R^{3a}$ and $R^{3b}$ are, independently, H or OH; and $R^X$ is H.

In some embodiments, X is unsubstituted 2-thienyl; and $R^1$, $R^4$, $R^{2a}$, $R^{2b}$, $R^{3a}$, $R^{3b}$, and $R^X$ are H.

In some embodiments, the compound of formula I, or pharmaceutically acceptable salt thereof, is present within a pharmaceutical composition comprising a pharmaceutically acceptable carrier.

In some embodiments, the inflammatory disease or condition is delayed-type hypersensitivity, contact dermatitis, atopic dermatitis, or septic shock.

DETAILED DESCRIPTION OF EMBODIMENTS

Figure 1:
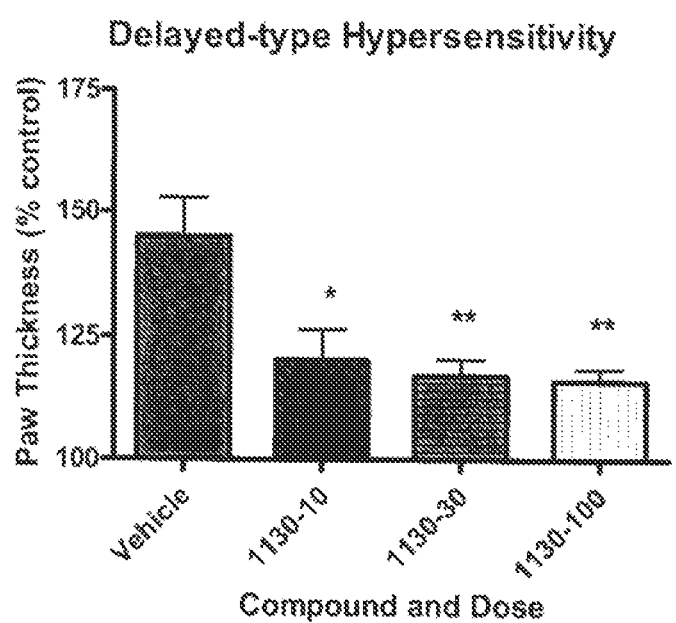
FIG. 1 is a bar graph depicting paw swelling in mice after sheep red blood cell challenge following administration of various amounts of tenilsetam.

As used herein, the singular forms "a", "an", and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 50% means in the range of 45%-55%.

The term "animal" as used herein includes, but is not limited to, humans and non-human vertebrates such as wild, domestic and farm animals.

As used herein and unless otherwise indicated, the phrase "compounds of the invention" means, collectively, compounds of formula I. These compounds are also referred to herein as "tenilsetam-related compounds." The compounds of the invention are identified herein by their chemical structure and/or chemical name. Where a compound is referred to by both a chemical structure and a chemical name, and that chemical structure and chemical name conflict, the chemical structure is determinative of the compound's identity.

The compounds of the present invention also include pharmaceutically acceptable salts of the compounds disclosed herein. As used herein, the phrase "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. In addition, a pharmaceutically acceptable carrier, diluent or excipient is compatible with the other ingredients of the formulation and not deleterious to the recipient thereof. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found, for example, in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

In some embodiments, the acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

In some embodiments, the compounds of Formula I may be present in the form of a prodrug. As used herein, "prodrug" refers to a moiety that releases a compound of the invention when administered to a patient. Prodrugs can be prepared by modifying functional groups present in the compounds in such a way that the modifications are cleaved, either in routine manipulation or in vivo, to the parent compounds. Examples of prodrugs include compounds of the invention as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds of the invention. Preparation and use of prodrugs is discussed in T. Higuchi et al., "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference in their entireties.

As may be appropriate, the compounds in this invention may contain one or more asymmetric centers, which can thus give rise to optical isomers (enantiomers) and diastereomers. While shown without respect to the stereochemistry in Formula I, the present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N.Y., 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that this invention may encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

As may be appropriate, one skilled in the art will also recognize that it is possible for tautomers to exist for the compounds of the present invention. The present invention includes all such tautomers even though not shown in the formulas herein.

The compounds of the invention also include the solvate and hydrate forms of the compounds. Compounds of the invention can also include all isotopes of atoms occurring in the intermediates or final compounds. Isotopes include those atoms having the same atomic number but different mass numbers. For example, isotopes of hydrogen include tritium and deuterium.

The compounds of the invention may also be double-bond isomers (i.e., geometric isomers).

When administered to a mammal (e.g., to an animal for veterinary use or to a human for clinical use) the compounds of the invention can be administered in isolated form. As used herein, "isolated" means that the compounds of the invention are separated from other components of either (a) a natural source, such as a plant or cell, preferably bacterial culture, or (b) a synthetic organic chemical reaction mixture, preferably, via conventional techniques, the compounds of the invention are purified. As used herein, "purified" means that when isolated, the isolate contains at least 90%, at least 95%, at least 98%, or at least 99% of a compound of the invention by weight of the isolate.

The term "improves" is used to convey that the present invention changes either the appearance, form, characteristics and/or the physical attributes of the tissue to which it is being provided, applied or administered. For example, with respect to the skin, the change in form may be demonstrated by any of the following alone or in combination: enhanced appearance of the skin; increased softness of the skin; increased turgor of the skin; decreased redness; and decreased swelling.

The term "inhibiting" includes the administration of a compound of the present invention to prevent the onset of the symptoms, alleviating the symptoms, or eliminating the disease, condition or disorder.

As used herein and unless otherwise indicated, the term "modulate" refers to a change in the expression and/or activity of a protein, an enzyme, a cell, or a target involved in the disease/disorder pathway. In an illustrative embodiment, "modulate" refers to the increase or decrease of the expression and/or activity of a antigen-specific, cell-mediated immune cells, such as T-cells.

Unless otherwise indicated, the term "skin" means that outer integument or covering of the body, consisting of the dermis and the epidermis and resting upon subcutaneous tissue.

As used herein and unless otherwise indicated, the phrase "therapeutically effective amount" of a composition of the invention is measured by the therapeutic effectiveness of a compound of the invention, wherein at least one adverse effect of a disorder is ameliorated or alleviated. In one embodiment, the phrase "therapeutically effective amount" of a composition of the invention is measured by the therapeutic effectiveness of a compound of the invention to alter the expression and/or activity of immune cells, including, but not limited to T-cells or T-cell mediated reactions.

The term "tissue" refers to any aggregation of similarly specialized cells which are united in the performance of a particular function.

"Treatment" or "treating" refers to an amelioration of a disease or disorder, or at least one discernible symptom thereof, preferably associated with an immune reaction or inflammatory reaction. Treatment also refers to an amelioration of at least one measurable physical parameter, not necessarily discernible by the patient. Treatment may also include inhibiting the progression of a disease or disorder, either physically, e.g., stabilization of a discernible symptom, physiologically, e.g., stabilization of a physical parameter, or both.

In some embodiments, the compounds of the invention are administered to a mammal in need thereof. That is, the compounds of the invention are administered to a mammal who has been identified as needing anti-inflammatory treatment.

One embodiment of the present invention encompasses compounds that are effective in modulating the expression and/or activity of immune cells both in vitro and in vivo.

In some embodiments, the present invention provides methods of treating or preventing an inflammatory disease or condition in a mammal comprising administering to the mammal a prophylactically or therapeutically effective amount of a compound of formula I

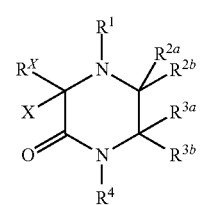

or a pharmaceutically acceptable salt thereof.

In some embodiments, X is 2-thienyl, 3-thienyl, 2-furyl, 3-furyl, or phenyl, each unsubstituted, mono-substituted, di-substituted, or tri-substituted with, independently, OH, halogen, $C_1$-$C_4$ alkyl, $C_1$-$C_4$ alkoxy, or ($C_1$-$C_4$) alkoxy-($C_1$-$C_4$) alkyl, or any subgroup thereof.

In some embodiments, X is 2-thienyl, 3-thienyl, 2-furyl, or 3-furyl, each unsubstituted, mono-substituted, di-substituted, or tri-substituted with, independently, OH, halogen, $C_1$-$C_4$ alkyl, $C_1$-$C_4$ alkoxy, or ($C_1$-$C_4$) alkoxy-($C_1$-$C_4$) alkyl, or any subgroup thereof.

In some embodiments, X is 2-thienyl, 3-thienyl, 2-furyl, or 3-furyl, each unsubstituted, mono-substituted, or di-substituted with, independently, OH, halogen, $C_1$-$C_4$ alkyl, or $C_1$-$C_4$ alkoxy, or any subgroup thereof.

In some embodiments, X is 2-thienyl or 2-furyl, each unsubstituted, mono-substituted, or di-substituted with, independently, OH, halogen, or $C_1$-$C_4$ alkyl, or any subgroup thereof.

In some embodiments, X is unsubstituted 2-thienyl or 2-thienyl mono-substituted with OH, halogen, or $C_1$-$C_4$ alkyl, or any subgroup thereof.

In some embodiments, X is unsubstituted 2-thienyl.

As used herein, the phrase "$C_1$-$C_4$" means branched or unbranched alkyl groups having from 1 to 4 carbons, such as, for example, methyl, ethyl, propyl, isopropyl, butyl, sec-butyl, tert-buyl.

As used herein, the term "halogen" means F, Cl, I, or Br.

In some embodiments, $R^1$ and $R^4$ are, independently, H or $C_1$-$C_4$ alkyl. In some embodiments, $R^1$ and $R^4$ are H. In some embodiments, $R^1$ and $R^4$ are $C_1$-$C_4$ alkyl.

In some embodiments, $R^{2a}$ and $R^{2b}$ are, independently, H, OH, or $C_1$-$C_4$ alkyl, or, together, $R^{2a}$ and $R^{2b}$ are C=O, or any subgroup thereof. In some embodiments, $R^{2a}$ and $R^{2b}$ are, independently, H or $C_1$-$C_4$ alkyl, or, together, $R^{2a}$ and $R^{2b}$ are C=O, or any subgroup thereof. In some embodiments, $R^{2a}$ and $R^{2b}$ are, independently, H or OH. In some embodiments, $R^{2a}$ and $R^{2b}$ are both H.

In some embodiments, $R^{3a}$ and $R^{3b}$ are, independently, H, OH, or $C_1$-$C_4$ alkyl, or, together, $R^{3a}$ and $R^{3b}$ are C=O, or any subgroup thereof. In some embodiments, $R^{3a}$ and $R^{3b}$ are, independently, H or $C_1$-$C_4$ alkyl, or, together, $R^{3a}$ and $R^{3b}$ are C=O, or any subgroup thereof. In some embodiments, $R^{3a}$ and $R^{3b}$ are, independently, H or OH. In some embodiments, $R^{3a}$ and $R^{3b}$ are both H.

In some embodiments, $R^X$ is H, $C_1$-$C_4$ alkyl, $C_1$-$C_4$ alkoxy, or ($C_1$-$C_4$) alkoxy-($C_1$-$C_4$) alkyl, or any subgroup thereof. In some embodiments, $R^X$ is H, $C_1$-$C_4$ alkyl, or $C_1$-$C_4$ alkoxy, or any subgroup thereof. In some embodiments, $R^X$ is H or $C_1$-$C_4$ alkyl. In some embodiments, $R^X$ is H.

In some embodiments, X is 2-thienyl, 3-thienyl, 2-furyl, 3-furyl, or phenyl, each unsubstituted, mono-substituted, di-substituted, or tri-substituted with, independently, OH, halogen, $C_1$-$C_4$ alkyl, $C_1$-$C_4$ alkoxy, or ($C_1$-$C_4$) alkoxy-($C_1$-$C_4$) alkyl, or any subgroup thereof $R^1$ and $R^4$ are, independently, H or $C_1$-$C_4$ alkyl; $R^{2a}$ and $R^{2b}$ are, independently, H, OH, or $C_1$-$C_4$ alkyl, or, together, $R^{2a}$ and $R^{2b}$ are C=O, or any subgroup thereof $R^{3a}$ and $R^{3b}$ are, independently, H, OH, or $C_1$-$C_4$ alkyl, or, together, $R^{3a}$ and $R^{3b}$ are C=O, or any subgroup thereof and $R^X$ is H, $C_1$-$C_4$ alkyl, $C_1$-$C_4$ alkoxy, or ($C_1$-$C_4$)alkoxy-($C_1$-$C_4$) alkyl, or any subgroup thereof.

In some embodiments, X is 2-thienyl, 3-thienyl, 2-furyl, or 3-furyl, each unsubstituted, mono-substituted, or di-substituted with, independently, OH, halogen, $C_1$-$C_4$ alkyl, or $C_1$-$C_4$ alkoxy, or any subgroup thereof; $R^1$ and $R^4$ are, independently, H or $C_1$-$C_4$ alkyl; $R^{2a}$ and $R^{2b}$ are, independently, H, OH, or $C_1$-$C_4$ alkyl, or, together, $R^{2a}$ and $R^{2b}$ are C=O, or any subgroup thereof; $R^{3a}$ and $R^{3b}$ are, independently, H, OH, or $C_1$-$C_4$ alkyl, or, together, $R^{3a}$ and $R^{3b}$ are C=O, or any subgroup thereof and $R^X$ is H, $C_1$-$C_4$ alkyl, or $C_1$-$C_4$ alkoxy, or any subgroup thereof.

In some embodiments, X is 2-thienyl or 2-furyl, each unsubstituted, mono-substituted, or di-substituted with, independently, OH, halogen, or $C_1$-$C_4$ alkyl, or any subgroup thereof; $R^1$ and $R^4$ are H; $R^{2a}$ and $R^{2b}$ are, independently, H or OH; $R^{3a}$ and $R^{3b}$ are, independently, H or OH; and $R^X$ is H.

In some embodiments, X is unsubstituted 2-thienyl or 2-thienyl mono-substituted with OH, halogen, or $C_1$-$C_4$ alkyl, or any subgroup thereof; $R^1$ and $R^4$ are H; $R^{2a}$ and $R^{2b}$ are, independently, H or OH; $R^{3a}$ and $R^{3b}$ are, independently, H or OH; and $R^X$ is H.

In some embodiments, X is unsubstituted 2-thienyl or 2-thienyl mono-substituted with OH, halogen, or $C_1$-$C_4$ alkyl, or any subgroup thereof; $R^1$ and $R^4$ are H; $R^{2a}$ and $R^{2b}$ are H; $R^{3a}$ and $R^{3b}$ are H; and $R^X$.

In some embodiments, X is unsubstituted 2-thienyl or 2-thienyl mono-substituted with OH or $C_1$-$C_4$ alkyl, or any subgroup thereof; and $R^1$, $R^4$, $R^{2a}$, $R^{2b}$, $R^{3a}$, $R^{3b}$, and $R^X$ are H.

In some embodiments, X is unsubstituted 2-thienyl; and $R^1$, $R^4$, $R^{2a}$, $R^{2b}$, $R^{3a}$, $R^{3b}$, and $R^X$ are H. Such a compound, known as tenilsetam, is (+/−)-3-(2-thienyl)-2-piperazinone and its chemical structure is depicted below.

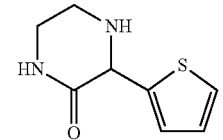 [SMILES: O=C1NCCNC1c1cccs1]

In certain embodiments, the compositions or compounds of the invention are administered to a patient, preferably a human, as a preventative measure against such diseases or conditions referred to herein. As used herein, "prevention" or "preventing" refers to a reduction of the risk of acquiring a given disease or condition. In some embodiments, the compositions or compounds of the present invention are administered as a preventative measure to a patient, preferably a human, having delayed-type hypersensitivity reactions, dermatitis, contact dermatitis, atopic dermatitis, or other conditions involving inflammation.

In some embodiments, the compound of formula I, or pharmaceutically acceptable salt thereof, is present within a pharmaceutical composition comprising a pharmaceutically acceptable carrier, as described herein.

In some embodiments, the inflammatory disease or condition is selected from delayed-type hypersensitivity, contact dermatitis, atopic dermatitis, or septic shock.

Diseases or conditions that are not contemplated to be within the scope of the present invention, and are thus not included within the claimed invention, include: Alzheimer's disease and Parkinson's disease or other such diseases characterized by accumulation of advanced glycation end products (AGEs) or any inflammation associated therewith, skin aging, diabetes, early diabetic retinopathy, cerebral hypoxia, cognitive dysfunction, aging, learning deficiency, memory deficiency, blood platelet aggregation diseases or conditions, thrombosis, nephritis, allergies such as asthma, pain, convulsive disorders, neurodegeneration, epilepsy, seizure, ictogenesis, epileptogenesis, hypertension, and viral infections.

Due to the activity of the compounds of the invention, the compounds are advantageously useful in veterinary and human medicine. As described above, the compounds of the invention are useful for the treatment or prevention of disease and disorders associated with immune and/or inflammatory reactions.

The invention provides methods of treatment and prophylaxis by administration to a patient of a therapeutically effective amount of a composition comprising a compound of the invention. The patient is a mammal, including, but not limited, to an animal such a cow, horse, sheep, pig, chicken, turkey, quail, cat, dog, mouse, rat, rabbit, guinea pig, or human, or any subgroup thereof. In some embodiments, the mammal is a human.

The present compositions, which comprise one or more compounds of the invention, can be administered topically.

The topical composition of the present invention can be a cosmetic, cosmeceutical, pharmaceutical or dermatological preparation that is applied to the skin as a topical cream or liquid solution or dispersion. However, the physical form of the topical composition is not critical. The compositions can also be, for example, formulated as bars, liquids, pastes, mousses, creams, gels, aerosols, lotions, hair shampoos, hair lotions, foam baths, shower baths, alcoholic and aqueous/alcoholic solutions, emulsions, wax/fat compounds, stick preparations, powders or ointments.

The topical compositions of the present invention can be formulated to have a pH which is similar to the pH of the skin. As such, neutral or slightly acidic pH's are suitable. In particular, the topical compositions of the present invention are formulated to have pH of between 4 and 7, or between 4.5 and 5.5.

The topical compositions can be applied by spreading or wiping the composition on the skin, or by spraying, dusting, dipping or otherwise exposing the skin to the topical composition.

In some embodiments, the skin is treated in a non-aerosol manner in order to avoid promotion of the evaporation of the components. Further, the topical compositions can be stored and/or used in a fashion which minimizes contact with the air before application to the skin.

The "cosmetic, dermatological or pharmaceutically acceptable carrier", as used herein, means one or more compatible solid or liquid filler diluents or microencapsulating substances which are suitable for administration to a human or lower animal. Suitable "carriers" should be of sufficiently high purity and sufficiently low toxicity to render them suitable for administration to the human or lower animal being treated. A safe and effective amount of carrier is from about 50% to about 99.5%, from about 70% to about 99%, or from about 80% to about 90%, of the composition.

Variations in formulation of these carriers may result in a wide variety of products which fall within the scope of the present invention.

The topical compositions of the present invention may be made into a wide variety of product types. These include, but are not limited to lotions, creams, beach oils, gels, sticks, sprays, ointments, pastes, mousses and cosmetics. These product types may comprise several types of carrier systems including, but not limited to solutions, emulsions, gels and solids.

The topical composition of the present invention formulated as solutions typically include a cosmetic, dermatological or pharmaceutically acceptable aqueous or organic solvent. The terms "solvent" refers to a material which is capable of having dispersed or dissolved therein the active compounds (namely, the free radical scavenger and the reactive carbonyl scavenger), and possesses acceptable safety properties (e.g., with respect to irritation and sensitization characteristics of the skin). Water is a typical aqueous solvent. Examples of suitable organic solvents include, but are not limited to: propylene glycol, butylene glycol, polyethylene glycol (200-600), polypropylene glycol (425-2025), glycerol, 1,2,4-butanetriol, sorbitol esters, 1,2,6-hexanetriol, ethanol, isopropanol, butanediol, and mixtures thereof.

If the topical compositions of the present invention are formulated as an aerosol and applied to the skin as a spray-on, a propellant can be added to a solution composition. Examples of propellants useful herein include, but are not limited to, the chlorinated, fluorinated and chloro-fluorinated lower molecular weight hydrocarbons. A more complete disclosure of propellants useful herein can be found in Sagarin, Cosmetics Science and Technology, 2nd Edition, Vol. 2, pp. 443-465 (1972).

Topical compositions of the present invention may be formulated as a solution comprising an emollient. An example of a composition formulated in this way would be a beach oil product. Such compositions can contain from about 0.1% to about 10% of the active compounds and from about 2% to about 50% of a cosmetic, dermatological or pharmaceutically-acceptable emollient.

As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32-43 (1972), contains numerous examples of suitable materials.

A lotion can be made from a solution carrier system. Lotions can comprise from about 0.1% to about 10%, or from about 1% to about 5%, of the active compounds; from about 1% to about 20%, or from about 5% to about 10%, of an emollient; and from about 50% to about 90%, or from about 60% to about 80%, water.

Another type of product that may be formulated from a solution carrier system is a cream. A cream of the present invention can comprise from about 0.1% to about 10%, or from about 1% to about 5%, of the active compounds; from about 5% to about 50%, or from about 10% to about 20%, of an emollient, and from about 45% to about 85%, or from about 50% to about 75%, water. Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. A more complete disclosure of thickening agents useful herein can be found in Segarin, Cosmetics, Science and Technology, 2nd Edition, Vol. 1, pp. 72-73 (1972).

If the carrier is formulated as an emulsion, from about 1% to about 10%, or from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et al; U.S. Pat. No. 4,421,769, issued Dec. 20, 1983, Dixon et al.; and McCutcheon's Detergents and Emulsifiers, North American Edition, pages 317-324 (1986). Suitable emulsifiers are anionic or nonionic, although the other types may also be used.

Lotions and creams can be formulated as emulsions as well as solutions. Such lotions can comprise from about 0.1% to about 10%, or from about 1% to about 5%, of the active compounds; from about 1% to about 20%, or from about 5% to about 10%, of an emollient; from about 25% to about 75%, or from about 45% to about 95%, water; and from about 0.1% to about 10%, or from about 0.5% to about 5%, of an emulsifier. Such creams can comprise from about 0.1% to about 10%, or from about 1% to about 5%, of the active compounds; from about 1% to about 20%, or from about 5% to about 10%, of an emollient; from about 20% to about 80%, or from about 30% to about 70%, water; and from about 1% to about 10%, or from about 2% to about 5%, of an emulsifier.

Single emulsion topical preparations, such as lotions and creams, of the oil-in-water type and water-in-oil type are well-known in the cosmetic art and are useful in the present invention. Multiphase emulsion compositions, such as the water-in-oil-in-water type, as disclosed in U.S. Pat. No. 4,254,105, are also useful in the present invention. In general, such single or multiphase emulsions contain water, emollients and emulsifiers as essential ingredients.

Triple emulsion carrier systems comprising an oil-in-water-in-silicone fluid emulsion composition as disclosed in U.S. Pat. No. 4,960,764, are also useful in the present invention. This triple emulsion carrier system can be combined with from about 0.1% to about 10%, or from about 1% to about 5%, of the active compounds to yield the topical compositions of the present invention.

Another emulsion carrier system useful in the topical compositions of the present invention is a microemulsion carrier system. An example of such a system comprises from about 9% to about 15% squalane; from about 25% to about 40% silicone oil; from about 8% to about 20% of a fatty alcohol; from about 15% to about 30% of polyoxyethylene sorbitan mono fatty acid (commercially available under the trade name Tweens) or other nonionics; and from about 7% to about 20% water. This carrier system can be combined with from about 1% to about 5% of the active compounds.

If the topical compositions of the present invention are formulated as a gel or a cosmetic stick, a suitable amount of a thickening agent, as disclosed herein, can be added to a cream or lotion formulation.

The topical compositions of the present invention may also be formulated as makeup products such as foundations.

The topical compositions of the present invention may contain, in addition to the aforementioned components, a wide variety of additional oil-soluble materials and/or water-soluble materials conventionally used in topical compositions, at their art-established levels.

Various water-soluble materials may also be present in the compositions of this invention. These include humectants, proteins and polypeptides, preservatives and an alkaline agent. In addition, the topical compositions herein can contain conventional cosmetic adjuvants, such as dyes, opacifiers (e.g., titanium dioxide), pigments and perfumes.

The topical compositions of the present invention may also include a safe and effective amount of a penetration enhancing agent. A suitable amount of penetration enhancing agent is from about 1% to about 5% of the composition. Examples of useful penetration enhancers, among others, are disclosed in U.S. Pat. Nos. 4,537,776, 4,552,872, 4,557,934, 4,130,667, 3,989,816, 4,017,641, and 4,954,487.

Other conventional topical product additives may also be included in the compositions of the present invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions of the present invention. For example, vitamin A, and derivatives thereof, vitamin B2, biotin, pantothenic, vitamin D, vitamin E, and mixtures thereof may be used.

The topical compositions of the present invention may also comprise, in addition to the active compounds, a cosmetically-acceptable surfactant. The term "cosmetically-acceptable surfactant" refers to a surfactant or emulsifier which is not only an effective skin cleanser, but also can be used without undue toxicity, irritation, allergic response, and the like. Furthermore, the surfactant or emulsifier should be capable of being commingled with the active compounds in a manner such that there is no interaction which would substantially reduce the efficacy of the composition for regulating skin wrinkles and/or skin atrophy.

The topical compositions of the present invention may contain from about 0.1% to about 20%, or from about 1% to about 5%, of the active compounds and from about 1% to about 90%, or from about 5% to about 10%, of a cosmetically-acceptable surfactant.

The surfactant component of the compositions of the present invention are selected from anionic, nonionic, zwitterionic, amphoteric and ampholytic surfactants, as well as mixtures of these surfactants. Such surfactants are well-known to those skilled in the detergency art.

Typical examples of suitable mild, i.e. particularly cosmetic, dermatologically or pharmaceutically acceptable emulisifiers or surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, alpha-olefin sulfonates, ether carboxylic acids, alkyl oligoglucosides, fatty acid glucamides, alkylamidobetaines and/or protein fatty acid condensates. In some embodiments, these are based on wheat proteins.

When formulated as "cleaning compositions", the topical composition of the present invention can optionally contain, at their art-established levels, any additional suitable known materials which are conventionally used in skin cleansing compositions.

While the compositions described hereinabove might be used in any suitable format, as described hereinabove, the topical compositions of the present invention might additionally comprise any of a number of additional materials described hereinabove, or otherwise designed to provide acceptable application properties, or provide additional cosmetic, pharmaceutical or dermatological effects. These additional materials can be, for example, superfatting agents, pearlizing waxes, consistency factors, thickeners, polymer additives, silicone compounds or derivatives, fats, oils, waxes, stabilizers, biogenic agents, deodorizers, anti-dandruff agents, film formers, foam stabilizers, electrolytes, swelling agents, UV protection factors, hydrotropes, preservatives, bactericides, perfumes and/or perfume oils, antifoanis, dyes, pigments which have a coloring effect, moisturizers and/or humectants, insect repellents, self-tanning agents, solubilizers, germ inhibitors, anti-inflammatory agents, benofuran derivatives, retinoids, chelating agents, and the like as further auxiliaries and additives.

The compounds of the invention may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, including to the ears, nose, eyes, or skin. The desired mode of administration is left to the discretion of the practitioner, and will depend, in part, upon the site of the medical condition. In most instances, administration will result in the release of the compounds of the invention into the bloodstream.

In some embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, Science, 1990, 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compounds of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of the target of the compounds of the invention, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, Science 249:1527-1533) may be used.

The present compositions can contain a therapeutically effective amount of a compound of the invention, optionally more than one compound of the invention, which may be in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles can be sterile. Water is a suitable vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., U.S. Pat. No. 5,698,155). Other examples of suitable pharmaceutical vehicles are described in "Remington's Pharmaceutical Sciences" by A. R. Gennaro.

In some embodiments, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

The compositions of the invention may also be administered orally. Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 200 milligrams of a compound of the invention per kilogram body weight. In some embodiments of the invention, the oral dose is 0.01 milligram to 70 milligrams per kilogram body weight, or 0.1 milligram to 50 milligrams per kilogram body weight, or 0.5 milligram to 20 milligrams per kilogram body weight, or 1 milligram to 10 milligrams per kilogram body weight. In some embodiments, the oral dose is 5 milligrams of a compound of the invention per kilogram body weight. The dosage amounts described herein refer to total amounts administered; that is, if more than one compound of the invention is administered, the preferred dosages correspond to the total amount of the compounds of the invention administered. Oral compositions can contain 10% to 95% active ingredient by weight.

Suitable dosage ranges for intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In some embodiments, the kit contains more than one compound of the invention. In another embodiments, the kit comprises a compound of the invention and another lipid-mediating compound, including but not limited to a statin, a thiazolidinedione, or a fibrate.

The compounds of the invention can be assayed in vitro and in vivo, for the desired therapeutic or prophylactic activity, prior to use in humans. For example, in vitro assays can be used to determine whether administration of a specific compound of the invention or a combination of compounds of the invention is suitable for lowering fatty acid synthesis. The compounds of the invention may also be demonstrated to be effective and safe using animal model systems.

In certain embodiments of the invention, the compounds of the invention can be used in combination therapy with at least one other therapeutic agent. The compound of the invention and the therapeutic agent can act additively or, more preferably, synergistically. In some embodiments, a composition comprising a compound of the invention is administered concurrently with the administration of another therapeutic agent, which can be part of the same composition as the compound of the invention or a different composition.

In some embodiments, a composition comprising a compound of the invention is administered prior or subsequent to administration of another therapeutic agent. As many of the disorders for which the compounds of the invention are useful in treating are chronic disorders, in one embodiment combination therapy involves alternating between administering a composition comprising a compound of the invention and a composition comprising another therapeutic agent, e.g., to minimize the toxicity associated with a particular drug. The duration of administration of each drug or therapeutic agent can be, e.g., one month, three months, six months, or a year. In some embodiments, when a composition of the invention is administered concurrently with another therapeutic agent that potentially produces adverse side effects including but not limited to toxicity, the therapeutic agent can advantageously be administered at a dose that falls below the threshold at which the adverse side is elicited.

A safe and effective amount of an anti-inflammatory agent may therefore be added to the composition of the present invention, at levels of from about 0.1% to about 10%, or from about 0.5% to about 5% of the composition. The exact amount of anti-inflammatory agent to be used in the compositions will depend on the particular anti-inflammatory agency utilized due to the wide variation in potency of such agents.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fiuclorolone acetonide, fludrocortisone, flumethasone pivalate, fiuosinolone acetonide, fiuocinonide, flucortine butylester, fiuocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethaso[eta]e, preunisolone, preunisone, beclomethasone dipropionate, triamcinolone, and mixtures thereof may be used. A suitable steroidal anti-inflammatory for use in the present invention is hydrocortisone.

A second class of anti-inflammatory agents which is useful in the compositions of the present invention includes the non-steroidal anti-inflammatory agents. Specific non-steroidal anti-inflammatory agents useful in the composition of the present invention include, but are not limited to: the oxicams, salicylates, acetic acid derivatives, fenamates, propionic acid derivatives, and pyrazoles.

Mixtures of these non-steroidal anti-inflammatory agents may also be employed, as well as the pharmaceutically-acceptable salts and esters of these agents. For example, etofenamate, a fliifenamic acid derivative, is particularly useful for topical application. Of the nonsteroidal anti-inflammatory agents, ibuprofen, naproxen, flufenamic acid, mefenamic acid, meclofenamic acid, piroxicam and felbinac are suitable. In some embodiments, ibuprofen, naproxen, and flufenamic acid are suitable.

Another class of anti-inflammatory agents which are useful in the present invention are the anti-inflammatory agents disclosed in U.S. Pat. No. 4,708,966. This patent reports a class of nonsteroidal anti-inflammatory compounds which comprise specifically substituted phenyl compounds, especially substituted 2,6-di-tert-butyl phenol derivatives. For example, compounds selected from 4-(4'-pentyn-3'-one)-2,6-di-t-butylphenol; 4-(5'-hexynoyl)-2,6-di -t-butyl[rho]henol; 4-((S)-(31)-3'-methyl-5'-hexynoyl)-2,6-di-t-butylphenol; 4-((R)-(+)-3'-methyl-5'-hexynoyl)-2,6-di-t-butylphenol; and 4-(3', 3'-dimethoxypropionyl)-2,6-di-t-butylphenol are useful in the present invention.

Yet another class of anti-inflammatory agents which are useful in the present invention are those disclosed in U.S. Pat. No. 4,912,248 This patent reports compounds and diastereomeric mixtures of specific 2-naphthyl-containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)-naproxol-(S)-2-methyl butyrate, diasteromeric mixtures of (S)-naproxen-(S)-2-butyl ester and (S)-naproxen-(R)-2-butyl ester, and diasteromeric mixtures of (S)-naproxol-(R)-2-methyl butyrate and (S)-naproxol-(S)-2-methyl butyrate are useful in the present invention.

Finally, naturally derived, or so-called "natural" anti-inflammatory agents are useful in the present invention. For example, candelilla wax, alpha bisabolol, aloe vera, Manjistha (extracted from plants in the genus *Rubia*, particularly *Rubia Cordifolia*), and Guggal (extracted from plants in the genus *Commiphora*, particularly *Commiphora Mukul*), may be used.

The present invention is also directed to the use of a compound of formula I or a pharmaceutically acceptable salt thereof, as described above, in the preparation of a medicament for treating or preventing an inflammatory disease, as described herein.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to routine methods known to those skilled in the art, using commercially available reagents, except where otherwise noted. In addition, each embodiment disclosed herein can be combined with any other embodiment disclosed herein.

EXAMPLES

Example 1

DTH

In this study, tenilsetam was assessed for its ability to affect the delayed-type hypersensitivity (DTH) reactions. DTH reactions are antigen-specific cell-mediated immune responses that can mediate harmful (e.g., allergic dermatitis and autoimmunity) aspects of immune function. The immune reaction induced by the method described below is characterized by swelling at the site of challenge and by an infiltration of monocytes/macrophages and lymphocytes into the epidermis and dermis. This model for skin DTH reactions has been used widely to monitor cell-mediated immune responses in vivo. Prednisolone (dexamethasone), a steroid anti-inflammatory, reduces cell-mediated immune responses and was employed to pharmacologically validate the assay.

Materials and Methods. ICR:CD1 male mice (Harlan) 12 to 13 weeks of age were used for this study. Animals were kept on a 12 hr light dark cycle and fed ad libitum. On day 1 of the study, mice were injected IV with $1 \times 10^6$ of washed sheep red blood cells in a volume of 200 µL. Mice were administered tenilsetam on day 6. Fifteen minutes after the day 6 drug treatment mice were injected with SRBC's ($1 \times 10^8$) in a volume of 25 µL into the back left footpad.

On day 7, mice were re-administered drug as above. Footpad thickness of both the back right and back left foot pads was measured using a digital micrometer. Foot pad thickness of the injected paw was normalized to the uninjected footpad for each animal. Visual observation for inflammatory conditions was utilized as well.

Data are expressed as the average±SEM. Data were averaged and analyzed by ANOVA followed by a post-hoc Tukey's test with a p value of less then 0.05 indicating a statistical difference.

For this study, there were 4 groups: vehicle, and tenilsetam at 3 dose levels: 10, 30 and 100 mg/kg. There were 6 animals per group.

Results. Tenilsetam significantly decreased foot swelling as measured using a micrometer and by visual examination. This occurred at all three doses (10, 30, 100 mg/kg) as shown in FIG. 1.

Example 2

Contact Hypersensitivity

Contact Hypersensitivity (Contact Dermatitis). Contact hypersensitivity (CHS)[3] is a T cell-mediated cutaneous immune/inflammatory reaction to haptens. Oxazolone can be used to evoke a contact hypersensitivity reaction and produce an animal model of contact dermatitis. Tenilsetam was assessed for its ability to affect oxazolone mediated contact dermatitis reaction.

Materials and Methods. ICR:CD1 male mice (Harlan) 12 to 13 weeks of age were used for this study. Animals were kept on a 12 hr light dark cycle and fed ad libitum.

Oxazolone sensitization. Mice were exposed to 50 µL of 3% oxazolone (in 100% ethanol) via topical application to the skin of the abdomen. Additional exposure was via the 4 paws with a small amount of oxazolone.

Oxazolone challenge. On day 5, both ears of mice were exposed to 1% oxazolone (20 µL per ear; 10 µL/side of ear).

Analysis. On day 6, ears were scored for redness on a 0-3 scoring basis and were measured for thickness using a micrometer. These values were recorded, group values were averaged and statistical differences determined by ANOVA followed by a Mann-Whitney U-test (for visual score) or by Tukey's test (for ear thickness). A p value of less than 0.05 was used to indicate statistical significance.

For this study, there were 5 groups: vehicle, and tenilsetam at 3 dose levels: 10, 30 and 100 mg/kg. In addition, there was a dexamethasone group. Dexamethasone functioned as the positive control for this study. There were 6 animals per group.

Figure 2A:
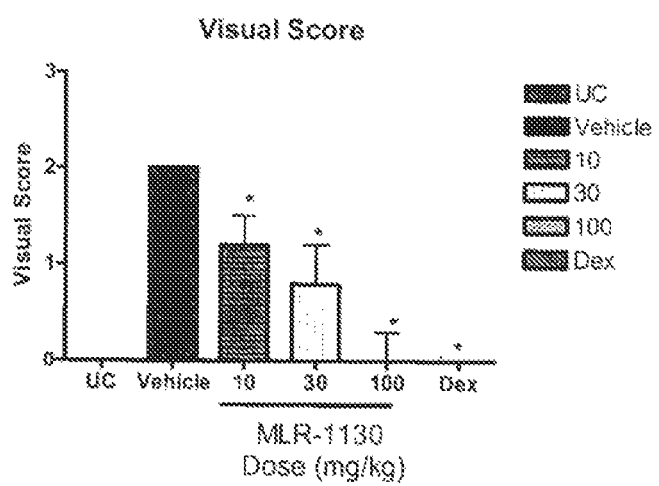
FIG. 2A is a bar graph of the visual score after skin and ear application of oxazolone following administration of various amounts of tenilsetam.
Figure 2B:
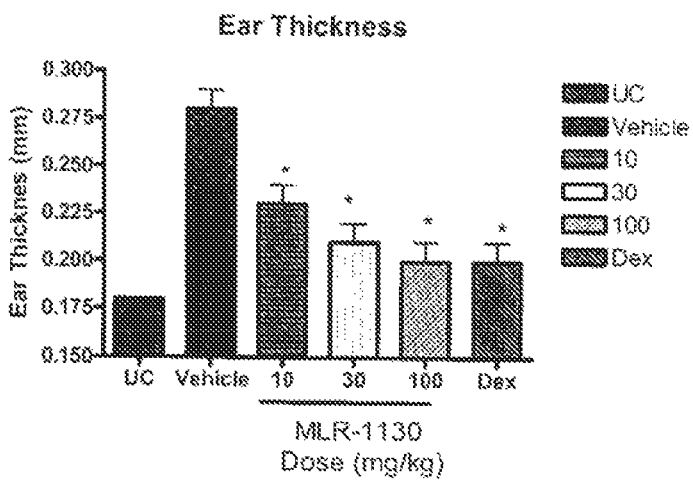
FIG. 2B is a bar graph of the measured ear thickness after skin and ear application of oxazolone following administration of various amounts of tenilsetam.

Results. Tenilsetam significantly decreased ear swelling after oxazolone challenge at all three doses measured. This affect was apparent with visual scoring and with ear thickness measurements, as depicted in FIG. 2.

Example 3

Septic Shock and Inflammation

Lipopolysaccharide General Inflammation. Bolus injection of lethal or sublethal doses of lipopolysaccharide (LPS; the major component of bacterial cell wall) results in the rapid and transient rise in tumor necrosis factor (TNFα) levels in serum in mammals. This animal model was developed to mirror certain aspects of septic shock in humans. This model is also an effective first-line general inflammation model and may be used to determine the anti-inflammatory potential of test compounds.

Materials and methods. Male ICR:CD1 mice (Harlan Sprague Dawley, Indianapolis, Ind.) 9 to 10 weeks of age were housed three per cage, kept on a standard 12 hr light cycle and fed western (high-fat) diet for 5.5 weeks for these studies. Mice were provided food and water ad libitum.

Lipopolysaccharide (heat killed *E. coli* 0127:B5; SigmaAldrich) was prepared in water at a concentration of 0.025 mg/ml. LPS was dosed at a volume of 10 ml/kg (ip) to produce a final dose of 0.25 mg/kg or 7.5 mg/mouse. Tenilsetam was dosed 15 minutes prior to LPS administration. Blood was collected by retrorbital eye bleed 90 minutes after LPS administration. Plasma was prepared from blood and TNFα levels determined by ELISA as described below.

Serum TNFα levels were determined using the OptEIA™ mouse TNFα ELISA kit (BD Biosciences) as per directions of the manufacturer. Data were averaged and analyzed by ANOVA followed by a post-hoc Tukey's test with a p value of less then 0.05 indicating a statistical difference.

For this study, there were 4 groups: vehicle, and Tenilsetam at 3 dose levels: 10, 30 and 100 mg/kg. There were 6 animals per group.

Figure 3:
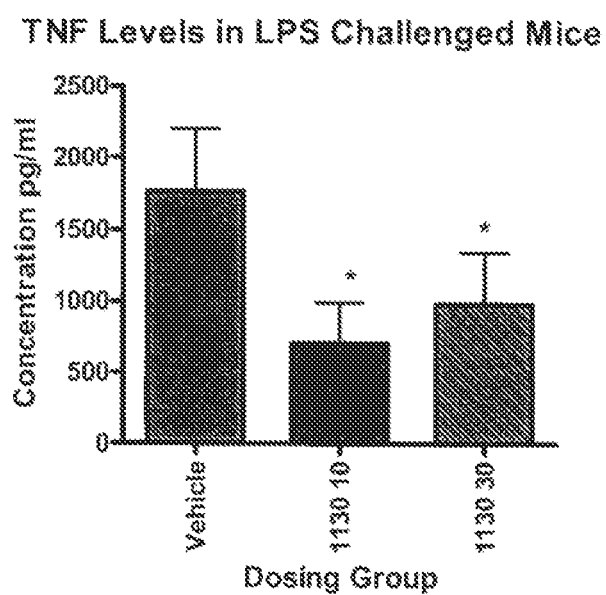
FIG. 3 is a bar graph of TNF levels in lipopolysaccharide challenged mice following administration of various amounts of tenilsetam.

Results. LPS administration in vehicle-treated mice increased serum TNF levels to approximately 1.8 μg/ml. Tenilsetam administration decreased TNFα levels at doses of 10 and 30 mg/kg as shown in FIG. 3.

The present invention is not to be limited in scope by the specific embodiments disclosed in the examples which are intended as illustrations of a few aspects of the invention and any embodiments which are functionally equivalent are within the scope of this invention.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, and the like) cited in the present application is incorporated herein by reference in its entirety.

What is claimed is:
1. A method of treating delayed-type hypersensitivity, contact dermatitis, atopic dermatitis, or septic shock in a human comprising administering to the human in need thereof a pharmaceutical composition comprising a therapeutically effective amount of a compound of formula I and pharmaceutically acceptable carrier, wherein:
X is 2-thienyl, 3-thienyl, 2-furyl, 3-furyl, or phenyl, each unsubstituted, mono-substituted, di-substituted, or tri-substituted with, independently, OH, halogen, $C_1$-$C_4$ alkyl, $C_1$-$C_4$ alkoxy, or ($C_1$-$C_4$) alkoxy-($C_1$-$C_4$) alkyl;
$R^1$ and $R^4$ are, independently, H or $C_1$-$C_4$ alkyl;
$R^{2a}$ and $R^{2b}$ are, independently, H, OH, or $C_1$-$C_4$ alkyl, or, together, $R^{2a}$ and $R^{2b}$ are C=O;
$R^{3a}$ and $R^{3b}$ are, independently, H, OH, or $C_1$-$C_4$ alkyl, or, together, $R^{3a}$ and $R^{3b}$ are C=O; and
$R^X$ is H, $C_1$-$C_4$ alkyl, $C_1$-$C_4$ alkoxy, or ($C_1$-$C_4$) alkoxy-($C_1$-$C_4$) alkyl;
or a pharmaceutically acceptable salt thereof, wherein the compound of formula I is administered in the absence of another therapeutic agent.

2. The method of claim 1 wherein X is 2-thienyl, 3-thienyl, 2-furyl, or 3-furyl, each unsubstituted, mono-substituted, or di-substituted with, independently, OH, halogen, $C_1$-$C_4$ alkyl, or $C_1$-$C_4$ alkoxy.

3. The method of claim 1 wherein X is unsubstituted 2-thienyl or 2-thienyl mono-substituted with OH, halogen, or $C_1$-$C_4$ alkyl.

4. The method of claim 1 wherein X is unsubstituted 2-thienyl.

5. The method of claim 1 wherein $R^1$ and $R^4$ are H or $C_1$-$C_4$ alkyl.

6. The method of claim 1 wherein $R^{2a}$ and $R^{2b}$ are, independently, H or $C_1$-$C_4$ alkyl, or, together, $R^{2a}$ and $R^{2b}$ are C=O.

7. The method of claim 1 wherein $R^{2a}$ and $R^{2b}$ are both H.

8. The method of claim 1 wherein $R^{3a}$ and $R^{3b}$ are, independently, H or $C_1$-$C_4$ alkyl, or, together, $R^{3a}$ and $R^{3b}$ are C=O.

9. The method of claim 1 wherein $R^{3a}$ and $R^{3b}$ are both H.

10. The method of claim 1 wherein $R^X$ is H, $C_1$-$C_4$ alkyl, or $C_1$-$C_4$ alkoxy.

11. The method of claim 1 wherein $R^X$ is H.

12. The method of claim 1 wherein:
X is unsubstituted 2-thienyl or 2-thienyl mono-substituted with OH, halogen, or $C_1$-$C_4$ alkyl;
$R^1$ and $R^4$ are, independently, H or $C_1$-$C_4$ alkyl;
$R^{2a}$ and $R^{2b}$ are, independently, H or OH;
$R^{3a}$ and $R^{3b}$ are, independently, H or OH; and
$R^X$ is H.

13. The method of claim 1 wherein:
X is unsubstituted 2-thienyl or 2-thienyl mono-substituted with OH, halogen, or $C_1$-$C_4$ alkyl; and
$R^1$, $R^4$, $R^{2a}$, $R^{2b}$, $R^{3a}$, $R^{3b}$, and $R^X$ are H.

14. The method of claim 1 wherein:
X is unsubstituted 2-thienyl; and
$R^1$, $R^4$, $R^{2a}$, $R^{2b}$, $R^{3a}$, $R^{3b}$, and $R^X$ are H.

15. The method of claim 1 wherein the pharmaceutical composition is administered to the human topically.

16. The method of claim 15 wherein the pharmaceutical composition is applied to the skin as a topical cream, liquid solution, or dispersion.

17. The method of claim 15 wherein the pharmaceutical composition is formulated as a bar, liquid, paste, mousse, cream, gel, aerosol, lotion, hair shampoo, hair lotion, beach oil, foam bath, shower bath, alcoholic and aqueous/alcoholic solution, emulsion, wax/fat compound, stick preparation, spray, powder, or ointment.

18. The method of claim 15 wherein the pharmaceutical composition further comprises an emollient, thickening agent, emulsifier, humectant, protein, preservative, alkaline agent, dye, opacifier, vitamin, pigment, perfume, penetration enhancing agent, or cosmetically-acceptable surfactant.

19. The method of claim 15 wherein the pharmaceutical composition further comprises collagen, hyaluronic acid, elastin, hydrolysate, primrose oil, jojoba oil, epidermal growth factor, soybean saponin, or mucopolysaccharide, or any mixture thereof.

20. The method of claim 5 wherein the pharmaceutical composition further comprises a superfatting agent, pearlizing wax, consistency factor, thickener, polymer additive, silicone compound, fat, oil, wax, stabilizer, biogenic agent, deodorizer, anti-dandruff agent, film former, foam stabilizer, electrolyte, swelling agent, UV protection factor, hydrotrope, preservative, bactericide, perfume, dye, pigment, moisturizer and/or humectant, insect repellent, self-tanning agent, solubilizer, germ inhibitor, benofuran derivative, retinoid, or chelating agent.

21. The method of claim 1 wherein the pharmaceutical composition is administered to the human orally.

22. The method of claim 21 wherein the pharmaceutical composition is formulated as a tablet, lozenge, aqueous or oily suspension, granule, powder, emulsion, capsule, syrup, or elixir.

23. The method of claim 21 wherein the pharmaceutical composition contains one or more agents chosen from a sweetening agent, a flavoring agent, a coloring agent, and a preserving agent.

* * * * *